United States Patent
Huth et al.

(10) Patent No.: US 10,786,687 B2
(45) Date of Patent: Sep. 29, 2020

(54) METHOD AND APPARATUS FOR PERFORMING IRRADIATION TIME OPTIMIZATION FOR INTENSITY MODULATED PROTON THERAPY DURING TREATMENT PLANNING WHILE MAINTAINING ACCEPTABLE IRRADIATION PLAN QUALITY

(71) Applicants: Varian Medical Systems Particle Therapy GmbH, Troisdorf (DE); Varian Medical Systems International AG, Cham (CH); Varian Medical Systems, Inc., Palo Alto, CA (US)

(72) Inventors: Isabel Huth, Kuerten (DE); Christel Smith, Santa Barbara, CA (US); Timo Koponen, Espoo (FI); Perttu Niemela, Espoo (FI); Markus Bach, Overath (DE); Reynald Vanderstraten, Brussels (BE)

(73) Assignees: Varian Medical Systems, Inc, Palo Alto, CA (US); Varian Medical Systems Particle Therapy GmbH, Troisdorf (DE); Varian Medical Systems International AG, Cham (CH)

( * ) Notice: Subject to any disclaimer, the term of this patent is extended or adjusted under 35 U.S.C. 154(b) by 0 days.

(21) Appl. No.: 16/147,110

(22) Filed: Sep. 28, 2018

(65) Prior Publication Data
US 2020/0105395 A1  Apr. 2, 2020

(51) Int. Cl.
*A61N 5/10* (2006.01)
*G16H 20/40* (2018.01)

(52) U.S. Cl.
CPC .... *A61N 5/1031* (2013.01); *A61N 2005/1087* (2013.01); *G16H 20/40* (2018.01)

(58) Field of Classification Search
None
See application file for complete search history.

(56) References Cited

U.S. PATENT DOCUMENTS 7,266,176 B2    9/2007  Allison et al.
2008/0242969 A1  10/2008  Sayeh et al.
(Continued)

FOREIGN PATENT DOCUMENTS

EP    3421085    1/2019

*Primary Examiner* — James Choi

(57) ABSTRACT

A computer implemented method of determining a resultant treatment plan for a proton radiation therapy system based on given dose volume constraints, wherein the resultant treatment plan is optimized for treatment time comprises accessing the dose volume constraints and range information, wherein the range information indicates acceptable deviations from the dose volume constraints. Based on the proton radiation therapy system, the method further comprises accessing machine configuration information comprising a plurality of machine parameters that define a maximum resolution achievable in irradiating a patient. Further, the method comprises iteratively adjusting the plurality of machine parameters to values which decrease the maximum resolution and simulating a plurality of candidate treatment plans to generate a plurality of treatment plan results, wherein each treatment plan result comprises: a respective treatment time and a respective plan quality. Finally, the method comprises selecting a resultant treatment plan with the shortest treatment time.

20 Claims, 9 Drawing Sheets

(56) References Cited

U.S. PATENT DOCUMENTS

| | | | |
|---|---|---|---|
| 2009/0041200 A1* | 2/2009 | Lu | A61N 5/1042 378/152 |
| 2013/0075622 A1* | 3/2013 | Katayose | A61N 5/1043 250/396 R |
| 2015/0095044 A1* | 4/2015 | Hartman | A61N 5/103 705/2 |
| 2015/0360057 A1* | 12/2015 | Balakin | A61N 5/1081 600/1 |
| 2018/0078789 A1 | 3/2018 | Ollila et al. | |

* cited by examiner

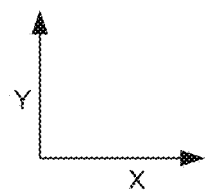
Fig. 5A
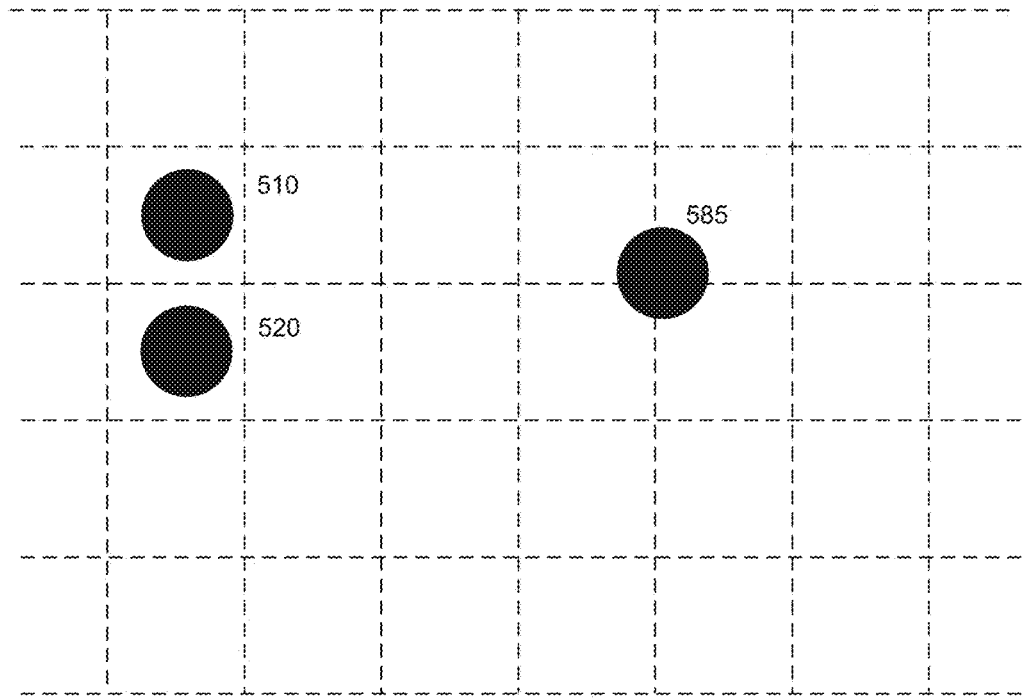
Fig. 5B
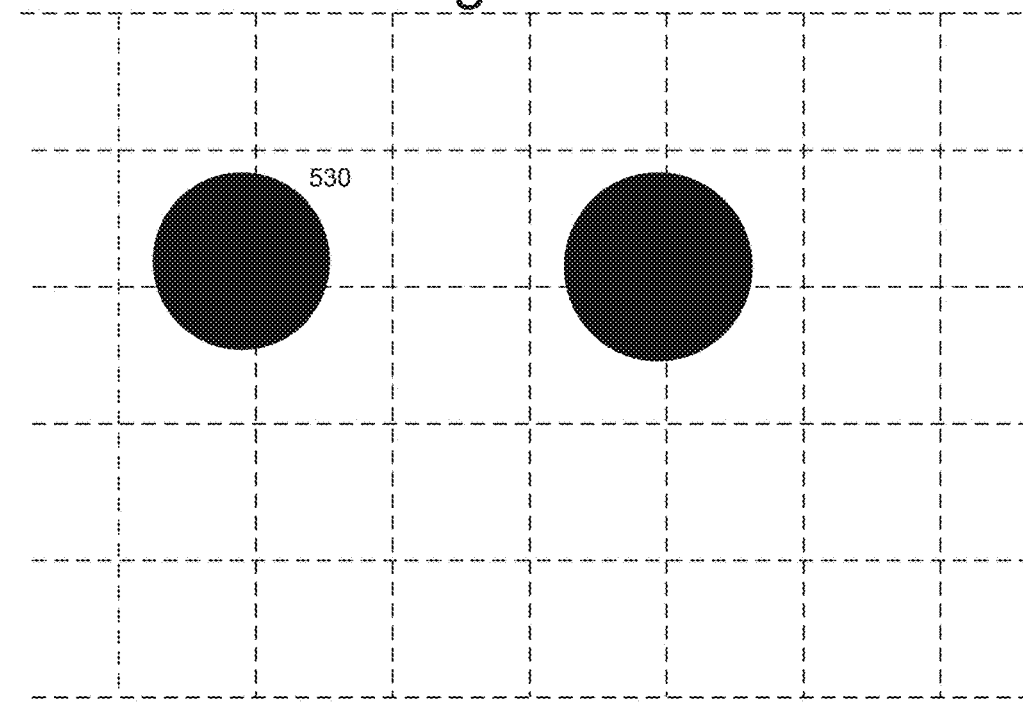

METHOD AND APPARATUS FOR PERFORMING IRRADIATION TIME OPTIMIZATION FOR INTENSITY MODULATED PROTON THERAPY DURING TREATMENT PLANNING WHILE MAINTAINING ACCEPTABLE IRRADIATION PLAN QUALITY

TECHNICAL FIELD

This description relates generally to the field of radiation therapy, and more particularly to optimizing performance of the therapy system in the execution of a radiation therapy treatment plan while maintaining acceptable plan quality.

BACKGROUND

Radiation therapy treatment plan development generally employs medical imaging, such as X-ray, computed tomography (CT), magnetic resonance imaging (MRI), or the like. Typically, a series of two-dimensional patient images, each representing a two-dimensional cross-sectional "slice" of the patient anatomy, are used to reconstruct a three-dimensional representation of a volume of interest (VOI), or structure of interest, from the patient anatomy.

The VOI typically includes one or more organs of interest, often including a planning target volume (PTV), such as a malignant growth or an organ including malignant tissue targeted for radiation therapy; a relatively healthy organ at risk (OAR) in the vicinity of a malignant growth at risk of radiation therapy exposure; or a larger portion of the patient anatomy that includes a combination of one or more PTVs along with one or more OARs. The objective of the radiation therapy treatment plan development typically aims to irradiate as much of the PTV as near the prescription dose as possible, while attempting to minimize irradiation of nearby OARs.

The resulting radiation therapy treatment plans are used during medical procedures to selectively expose precise areas of the body, such as malignant tumors, to specific doses of radiation in order to destroy the undesirable tissues. During the development of a patient-specific radiation therapy treatment plan, information generally is extracted from the three-dimensional model to determine parameters such as the shape, volume, location, and orientation of one or more PTVs along with one or more OARs.

Proton therapy is a type of external beam radiation therapy that is characterized by the use of a beam of protons to irradiate diseased tissue. Typically, radiation therapy involves directing a beam of high energy proton, photon, or electron radiation ("therapeutic radiation") into a target volume (e.g., a tumor or lesion). A chief advantage of proton therapy over other conventional therapies such as X-ray or neutron radiation therapies is that proton radiation can be limited by depth, and therefore the exposure to inadvertent radiation can be avoided or at least limited by non-target cells having a depth beyond a target calculated area.

A popular implementation of proton therapy uses monoenergetic pencil beams at varying energy levels, which are spot-scanned over a target area for one or more layers of depth. By superposition of several proton beams of different energies, a Bragg peak can be spread out to cover target volumes using a uniform, prescribed dose. This enables proton radiation applications to more precisely localize the radiation dosage relative to other types of external beam radiotherapy. During proton therapy treatment, a particle accelerator such as a cyclotron or synchrotron is used to generate a beam of protons from, for example, an internal ion source located in the center of the particle accelerator. The protons in the beam are accelerated (via a generated electric field), and the beam of accelerated protons is subsequently "extracted" and magnetically directed through a series of interconnecting tubes (called a beamline), often through multiple chambers, rooms, or even floors of a building, before finally being applied through a radiation application device at an end section of beam line (often through a radiation nozzle) to a target volume in a treatment room.

As the volumes (e.g., organs, or regions of a body) targeted for radiation therapy are often below the surface of the skin and/or extend in three dimensions, and since proton therapy—like all radiation therapies—can be harmful to intervening tissue located in a subject between the target area and the beam emitter, the precise calculation and application of correct dosage amounts and positions are critical to avoid exposing regions in the radiation subject outside the specific areas targeted to receive radiation.

Before a patient is treated with radiation, a treatment plan specific to that patient is developed. The plan defines various aspects of the therapy using simulations and optimizations based on past experiences. For example, for intensity modulated radiation therapy (IMRT), the plan can specify the appropriate beam type and the appropriate beam energy. Other parts of the plan can specify, for example, the angle of the beam relative to the patient, the beam shape, the placement of boluses and shields, and the like. In general, the purpose of the treatment plan is to deliver sufficient radiation to the target volume while minimizing exposure of surrounding healthy tissue to the radiation.

In IMRT, the planner's goal is to find a solution that is optimal with respect to multiple clinical goals that may be contradictory in the sense that an improvement toward one goal may have a detrimental effect on reaching another goal. For example, a treatment plan that spares the liver from receiving a dose of radiation may result in the stomach receiving too much radiation. These types of tradeoffs lead to an iterative process in which the planner creates different plans to find the one plan that is best suited to achieving the desired outcome. Furthermore, treatment planning software can be used to find an optimal plan that considers all the clinical goals and dosimetric criteria.

In proton therapy, short irradiation times are desirable. Patients must hold their breath during therapy on certain organs, particularly their lungs, to avoid the tumor moving in and out of the proton beam. Therefore, lung or liver cancer is typically treated with breath-holding techniques so as to minimize the interplay effects of moving targets. Delivering the required dose as quickly as possible therefore limits the amount of time that a patient needs to hold her breath.

One of the drawbacks of conventional commercially available treatment planning systems is that while they may, for example, be optimized according to certain dose volume constraints (for target volume and organs at risk) or according to plan robustness (to take inter or intra-fraction position inaccuracies into account), typically, conventional proton therapy systems do not consider temporal behavior of the beam application during optimization. That is to say, treatment plans are currently optimized for plan quality, e.g., optimized according to given dose volume constraints for target volume and organs at risk. More specifically, conventional treatment planning systems for proton therapy do not optimize for time by taking into account certain machine specific criteria (related to the proton therapy delivery system properties) that have a significant impact on irradiation times. In other words, conventional treatment planning systems do not optimize for delivery system machine-specific limitations—this results in prolonging irradiation times and increasing the probability of an interlock occurrence.

SUMMARY

Embodiments according to the present invention provide a methodology that performs time-based optimization during the course of treatment planning for intensity modulated proton therapy systems, in particular, by taking into account certain beam characteristics and configuration (or calibration) criteria pertaining to the physical constraints of machines delivering the proton therapy. In other words, embodiments according to the present invention create a treatment plan that is optimized for efficiency of performance (using certain radiation therapy beam and machine specific parameters) while simultaneously delivering a clinically acceptable plan quality (for dose distribution).

In one embodiment, a computer implemented method of determining a resultant treatment plan for a proton radiation therapy system based on given dose volume constraints, wherein the resultant treatment plan is optimized for treatment time is disclosed. The method comprises accessing the dose volume constraints and range information, wherein the range information indicates acceptable deviations from the dose volume constraints. Based on the proton radiation therapy system, the method also comprises accessing machine configuration information comprising a plurality of machine parameters that define a maximum resolution achievable by the proton radiation therapy system in irradiating a patient. Further, the method comprises iteratively adjusting the plurality of machine parameters to generate a plurality of candidate treatment plans, wherein the iteratively adjusting comprises adjusting the plurality of machine parameters to values which decrease the maximum resolution. Subsequently, the method comprises simulating the plurality of candidate treatment plans with respect to the proton radiation therapy system to generate a plurality of treatment plan results, wherein each treatment plan result comprises a respective treatment time and a respective plan quality. Finally, the method comprises selecting the resultant treatment plan from the plurality of candidate treatment plans, wherein the resultant treatment plan yields a treatment plan result comprising a shortest treatment time of the plurality of treatment plan results and an acceptable plan quality with respect to the dose volume constraints. Embodiments also include a computer system implemented to execute the method as described above.

Thus, embodiments according to the invention improve the field of radiation treatment planning specifically and the field of radiation therapy in general. In IMRT, beam intensity is varied across each treatment region (target volume) in a patient. Instead of being treated with a relatively large and uniform beam, the patient is treated with many smaller beams (e.g., pencil beams or beamlets), each of which can have its own intensity, and each of which can be delivered from a different angle (which may be referred to as beam geometry) to irradiate a spot. Because of the many possible beam geometries, the number of beams, and the range of beam intensities, there is effectively an infinite number of potential treatment plans, and therefore consistently and efficiently generating and evaluating high-quality treatment plans is beyond the capability of a human and requires the use of a computing system, particularly considering the time constraints associated with the use of radiation therapy to treat ailments like cancer, and particularly considering the large number of patients that are undergoing or need to undergo radiation therapy during any given time period.

Furthermore, performing a multi-directional optimization that optimizes a treatment plan for efficiency by considering complex machine and beam-specific parameters (e.g., minimal application monitor units per spot, energy layer spacing, spot size and spot spacing, etc.) without sacrificing plan quality is beyond the capability of a human and requires the use of a computing system. Embodiments according to the invention allow effective treatment plans with low treatment delivery times to be generated, which limit the possibility of irregularities or inaccuracies in treatment delivery due to patient movement. Also, embodiments according to the invention help improve the functioning of computing systems by improving system reliability and availability, which results from a lower likelihood of interlock occurrence.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIGS. 5A and 5B illustrate exemplary grids in the x-y plane over which proton therapy is delivered in accordance with an embodiment of the invention.

DETAILED DESCRIPTION

Figure 1:
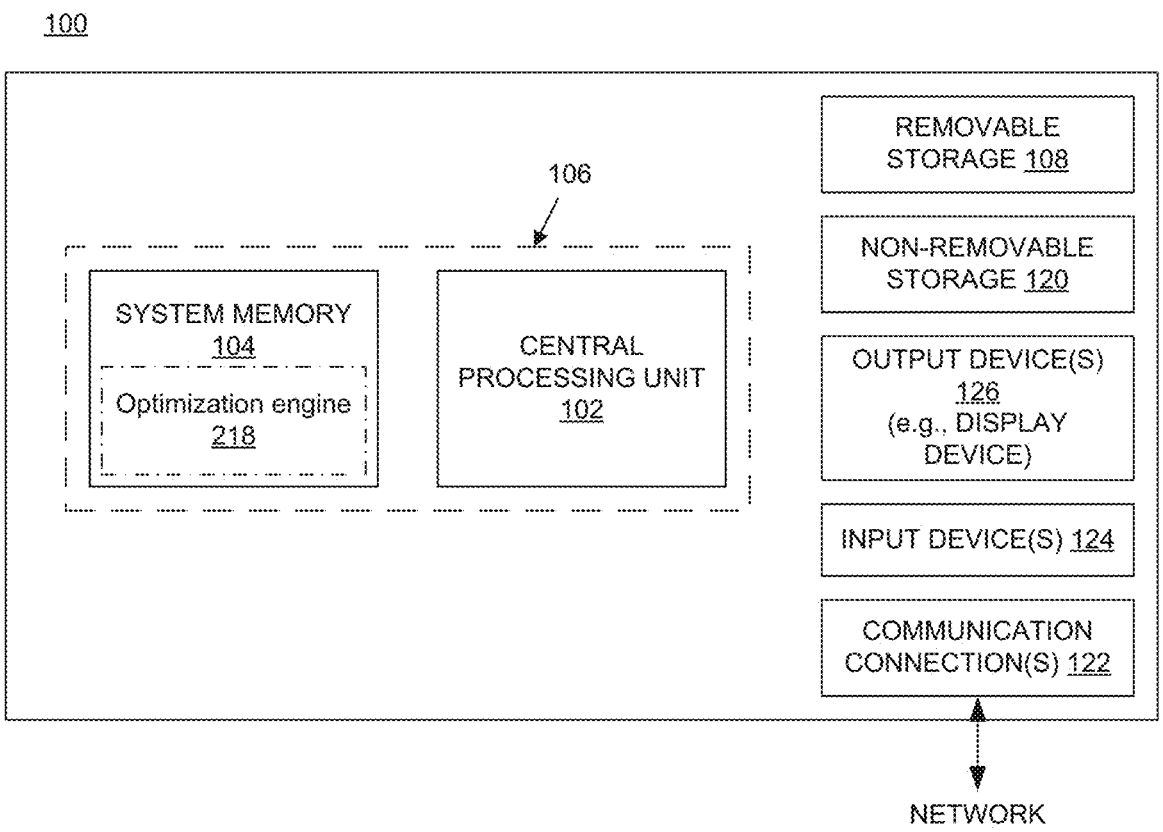
FIG. 1 shows a block diagram of an example of a computing system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computing system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "adjusting," "simulating," "selecting," "loading," and "using or the like, refer to actions and processes (e.g., the flowcharts of FIG. 8) of a computing system or similar electronic computing device or processor (e.g., the computing system 100 of FIG. 1). The computing system or similar electronic computing device manipulates and transforms data represented as physical (electronic) quantities within the computing system memories, registers or other such information storage, transmission or display devices.

Portions of the detailed description that follows are presented and discussed in terms of a method. Although steps and sequencing thereof are disclosed in figures herein (e.g., FIG. 8) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information and that can accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

This present disclosures provides a solution to the challenge inherent of reducing irradiation time during treatment delivery without sacrificing dose distribution (or treatment plan quality). In particular, various embodiments of the present disclosure provide a methodology that performs time-based optimization during the course of treatment planning for proton therapy systems, in particular, by taking into account characteristics of the proton delivery system (e.g., certain beam characteristics and configuration/calibration criteria pertaining to machines delivering the proton therapy.) In other words, embodiments according to the present invention create a treatment plan that is optimized for efficiency of performance (using certain radiation therapy beam and machine specific parameters) while simultaneously delivering a clinically acceptable plan quality (for dose distribution).

Conventional commercially available radiation treatment planning systems can be optimized according to given dose volume constraints for planning target volume (PTV) and organs at risk (OAR) and according to plan robustness (taking inter or intra-fraction position inaccuracies into account). Conventional treatment planning systems, however, do not take into account certain physical constraints or properties of the delivery system (e.g., certain beam characteristics or machine specific operation parameters and their limits) in the base data it considers in the performance of this optimization. Accordingly, even though conventional treatment planning systems may be able to produce a clinically acceptable treatment plan, the treatment plan developed may not use the full system or machine capability to make use of the system in the most efficient or reliable way to get the treatment delivered as planned. In other words, because certain delivery system specific parameters (e.g., pertaining to physical constraints of the beam machine) are fixed (and cannot be varied during treatment planning or while trying to establish the most optimal treatment plan), the treatment plans developed by conventional treatment planning systems, while being acceptable, may not be optimized for time and may, therefore, be inefficient. Accordingly, even if an optimized treatment plan in conventional systems passes the criteria for plan quality and treatment delivery time, the application at the radiation therapy beam machine may fail during delivery or may not have the optimal delivery efficiency as requested by plan objectives during treatment planning due to limitations specific to the beam machine capability (or machine-specific plan parameters) that are not taken into account by the currently available commercial treatment planning systems.

Accordingly, embodiments of the present invention account for and adjust certain delivery system specific parameters, e.g., beam energies, spot positions, global minimum spot intensities, and spot lateral spread (or spot size) in developing a performance optimized treatment plan that deliver the required plan quality. This allows embodiments of the present invention to perform a multi-directional optimization and deliver a treatment plan that simultaneously delivers a clinically acceptable plan quality (for dose distribution) with the shortest irradiation periods. By comparison, conventional treatment delivery systems, parameters associated with certain physical constraints, e.g., beam energies, spot positions, spot lateral spread, etc., are assumed to be fixed and cannot be optimized for in the development of a treatment plan.

In one embodiment, the present invention comprises a software based optimization engine that translates delivery system knowledge into treatment planning. The optimization engine provides a treatment plan with acceptable treatment plan quality (dose distribution) while optimizing for plan delivery efficiency (especially delivery time for all fields of a treatment plan) as well as delivery performance in general to improve system reliability and availability. Optimizing for efficiency (by taking into consideration radiation therapy beam machine specific behavior, thresholds and limitations) also reduces the probability of interlock occurrence. Accordingly, embodiments of the present invention are able to deliver treatment plans with the full capability of the treatment delivery system (TDS) with the highest possible efficiency. The optimization engine allows users of the TDS to take advantage of the radiation treatment delivery system and treatment planning system in a targeted manner by finding an optimal outcome for individual treatment (with respect to efficiency influencing variables pertaining to treatment delivery).

Embodiments of the present invention are advantageous because they allow optimal usage of machine capability—this reduces interlock occurrence, which can be managed and directly influenced during treatment planning. As a result of fewer interlocks, the delivery system is able to keep up with a created treatment plan and machine downtimes are avoided.

Further, the optimization engine of the present invention simultaneously ensures adequate treatment plan quality and tailors treatment delivery to take advantage of the maximum system capabilities of a TDS (including temporal behavior and reliability). Accordingly, embodiments of the present invention minimize overall irradiation times while maintaining limits that guarantee accurate beam position and dose application. Because treatment times are shorter, embodiments of the present invention support advanced breath-hold treatment planning. In other words, with shorter treatment times, the patient may not be required to hold their breath for longer periods of time, thereby, allowing the treatment to be delivered accurately while minimizing patient movement. Furthermore, machine load/wear is reduced because of the shorter irradiation times.

Additionally, optimizing for certain delivery system specific parameters, e.g., beam energies, spot positions, global minimum spot intensities, and spot lateral spread (or spot size) leads to more robust treatment plans. For example, varying spot positions and spot lateral spread may allow an acceptable dose to be applied using fewer spots. Optimizing over additional physical degrees of freedom may also lead to better results for the dosimetric criteria due to a qualitatively larger set of degrees of freedom available to the optimization engine. In particular, it leads to improved dose homogeneity for the target structure, e.g., the tumor.

Designing a more reliable system by taking certain machine degrees of freedom (e.g., beam energies, spot positions, global minimum spot intensities, and spot lateral spread) into consideration also prevents the designer of a treatment plan from having to re-design a treatment plan in case a prior one fails, e.g., as a result of an interlock. By providing increased degrees of freedom in the optimization process and making more optimal use of hardware capabilities, embodiments of the present invention are able to reduce delivery time, machine interlock probability and machine maintenance, without having a significant impact on the primary dosimetric objectives.

FIG. 1 shows a block diagram of an example of a computing system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as keyboard, mouse, pen, voice input device, touch input device, etc. Output device(s) 126 such as a display device, speakers, printer, etc., may also be included.

As will be explained further below, embodiments according to the invention utilize an optimization engine 218. In the example of FIG. 1, the memory 104 includes computer-readable instructions, data structures, program modules, and the like associated with the optimization engine 218. However, the optimization engine 218 may instead reside in any one of the computer storage media used by the system 100, or may be distributed over some combination of the computer storage media, or may be distributed over some combination of networked computers.

The optimization engine 218 is programmed to simultaneously optimize for performance efficiency while also taking into consideration treatment plan quality and tailor treatment delivery to take advantage of the maximum system capabilities of a TDS (including temporal behavior and reliability). In conventional treatment planning systems, the physical degrees of freedom specific to a machine, e.g., the number of available beam energies and steps between them, spot positions, spot lateral spread, etc. are fixed parameters. The optimization engine 218 allows the user to optimize for efficiency by varying physical degrees of freedom pertaining to the machine. By comparison, conventional treatment planning systems only use fixed parameters (that may be developed through trial and error) for the physical degrees of freedom e.g., the number of available beam energies and steps between them, spot positions, spot lateral spread, etc.

Figure 2:
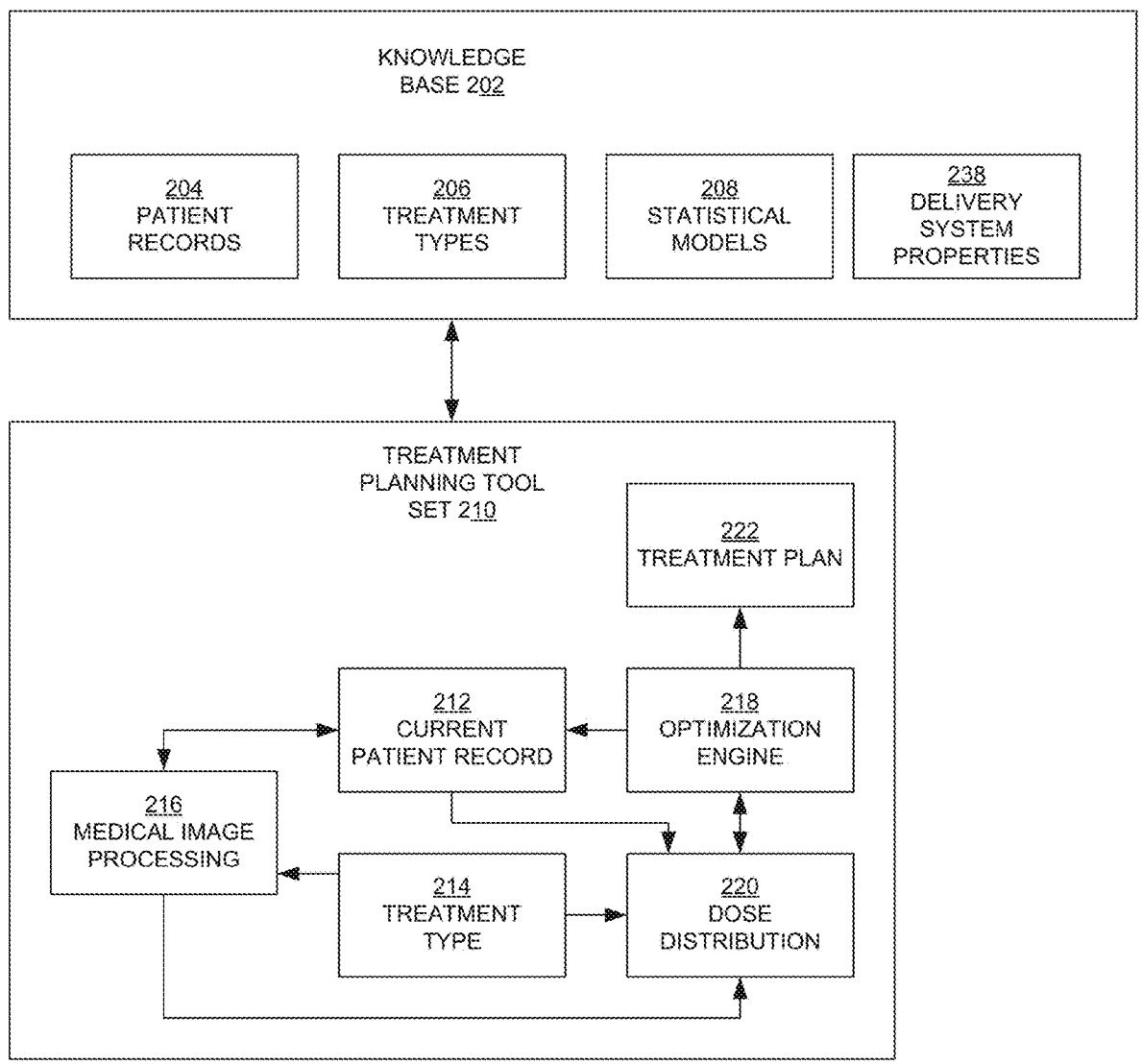
FIG. 2 illustrates an embodiment of a knowledge-based planning system incorporating a combination of dosimetric criteria and certain delivery system properties for generating radiation treatment plans in an embodiment according to the present invention.

FIG. 2 illustrates an embodiment of a knowledge-based planning system 200 incorporating a combination of dosimetric criteria and certain delivery system properties for generating radiation treatment plans in an embodiment according to the present invention. In the example of FIG. 2, the system 200 includes a knowledge base 202 and a treatment planning tool set 210. The knowledge base 202 includes patient records 204 (e.g., radiation treatment plans), treatment types 206, statistical models 208 and other dosimetric criteria for delivering an effective treatment plan. The knowledge base 202, in accordance with embodiments of the present invention, may also include certain delivery system properties 238 (e.g., the degrees of freedom that can be varied including the number of available energies and the steps between them, spot positions, spot intensities and spot lateral spread).

The treatment planning tool set 210 in the example of FIG. 2 includes a current patient record 212, a treatment type 214, a medical image processing module 216, an optimizer 218, a dose distribution module 220, and a final radiation treatment plan 222.

The treatment planning tool set 210 searches through the knowledge base 202 (through the patient records 204) for prior patient records that are similar to the current patient record 212. The statistical models 208 can be used to compare the predicted results for the current patient record 212 to a statistical patient. Using the current patient record 212, a selected treatment type 206, selected statistical models 208, and delivery system properties 238, the tool set 210 generates a radiation treatment plan 222 using the optimization engine 218 to optimize for several (potentially conflicting) objectives, e.g., time versus adequacy of dose distribution. A radiation treatment plan developed in this manner (e.g., the treatment plan 222) can be referred to as a balanced plan.

More specifically, based on past clinical experience, when a patient presents with a particular diagnosis, stage, age, weight, sex, co-morbidities, etc., there can be a treatment type that is used most often. By selecting the treatment type that the planner has used in the past for similar patients, a treatment type 214 can be chosen. The medical image processing module 216 provides automatic contouring and automatic segmentation of two-dimensional cross-sectional slides (e.g., from computed tomography or magnetic resonance imaging) to form a 3D image using the medical images in the current patient record 212. Dose distribution maps are calculated by the dose distribution module 220.

The knowledge base 202 can be searched for a combination of objectives that can be applied by the optimization engine 218 to determine a dose distribution. For example, an average organ-at-risk dose-volume histogram, a mean cohort organ-at-risk dose-volume histogram, and average organ-at-risk objectives can be selected from the knowledge base 202. In embodiments according to the present invention, the optimization engine 218 can optimize for certain delivery system specific parameters (from delivery system properties 238), e.g., the number of available energies and the steps between them, spot positions, spot intensities and spot lateral spread. As mentioned above, optimizing over additional physical degrees of freedom may also lead to better results for the dosimetric criteria or clinical goals due to a qualitatively larger set of degrees of freedom available to the optimization engine. In particular, it leads to improved dose homogeneity for the target structure, e.g., the tumor. Further, it leads to time optimization—an acceptable dose quality can be delivered in the fastest and most efficient manner possible.

By comparison, in conventional therapy systems, the only criteria considered were the static properties of the final dose distribution, which in effect determined the quality of the plan. Embodiments of the present invention, however, consider the time aspect of delivering the dose distribution as well. In other words, embodiments of the present invention enable an acceptable quality of treatment plan to be delivered in the most time efficient way.

Figure 3A:
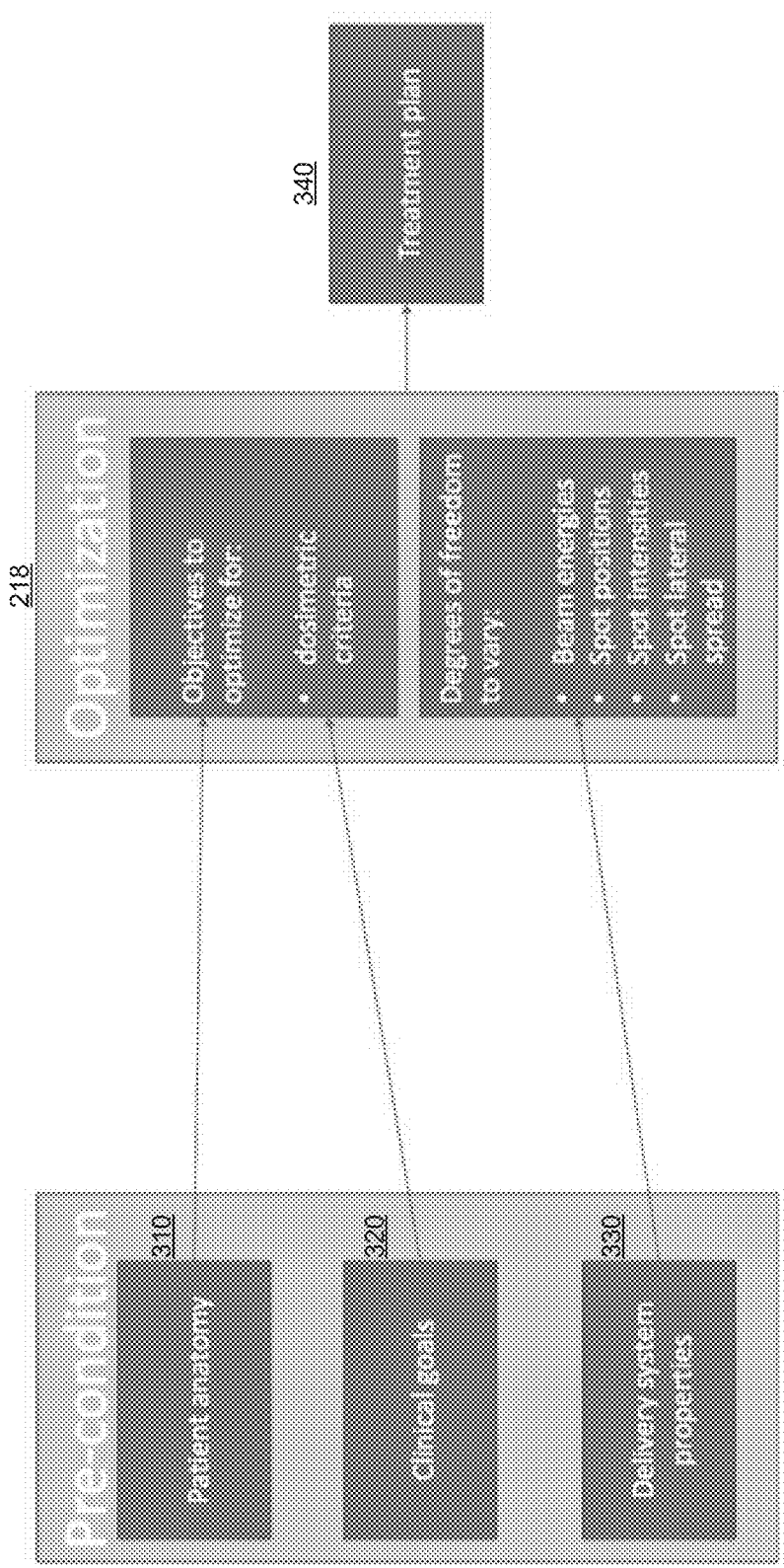
FIG. 3A illustrates a data flow diagram of a process that can be implemented to create a treatment plan that takes into consideration certain physical degrees of freedom in an embodiment according to the present invention.

FIG. 3A illustrates a process 300 that can be implemented to create a treatment plan that takes into consideration certain physical degrees of freedom in an embodiment according to the present invention. Process 300 can be implemented as computer-readable instructions stored in a computer-usable medium and executed on a computing system like the system 100 of FIG. 1.

The clinical goals 320 of FIG. 3A include (as computer-readable data) a clinical goal or set of clinical goals. In general, a clinical goal is a factor that is related to treatment outcome. The clinical goals offer leeway in the trade-off between the competing objectives of delivering doses to a target volume (e.g., diseased tissue) while minimizing doses to surrounding (e.g., healthy) tissue. Clinical goals 320 may also include an acceptable range of deviation from those goals and still yield an acceptable plan quality.

The clinical goals 320 are used to guide the development of a radiation treatment plan describing, among other parameters, the type of radiation to be used, the orientation of the radiation therapy beams to be directed toward patient at multiple beam stations, the shape for collimation of the beams, and the amount of dose to be delivered at each station. A clinical goal may also define constraints or goals for quality metrics such as minimum and maximum dose amounts and mean dose for particular tissue volumes (called regions of interest or ROIs), dose homogeneity, target volume dose distribution, organ-at-risk dose distributions, other normal tissue dose distributions, other spatial dose distributions, and other acceptable ranges of deviation.

Given the patient anatomy details 310 (also available in the knowledge base 202) and the clinical goals 320, the treatment planning system can optimize for the dosimetric criteria. For example, a dosimetric criterion may dictate a minimum number of Grays of radiation to be applied to a planning target volume (PTV) and a maximum number of Grays of radiation to be applied to an organ at risk (OAR). In other words, the dosimetric criteria may be considered a dose volume plan or dose distribution plan that determines the manner in which the dose is distributed over the three dimensional space being treated.

Embodiments of the present invention comprise an optimization engine 218 that delivers an acceptable treatment plan quality (for a given dosimetric criteria) while optimizing for delivery system properties 330 (e.g., various degrees of physical freedom associated with a treatment delivery system) to develop a treatment plan 340. As mentioned above, conventional treatment systems were only able to optimize for the dosimetric criteria. By comparison, embodiments of the present invention allow the user to optimize for efficiency by varying physical degrees of freedom pertaining to the machine, e.g., the number of available beam energies and steps between them, spot positions, spot lateral spread, etc.

In one embodiment, the treatment planning software may receive as inputs machine configuration such as the maximum and minimum range for each of the various machine specific parameters, e.g., a maximum and minimum depth of the target structure for determining layer spacing, a maximum and minimum number of monitor units (MUs) per spot that a beam machine can deliver, a maximum and minimum spot size (or spot lateral spread), and a maximum and minimum breadth of the target structure for determining spot positioning. Given the ranges for each of the parameters, the optimization engine 218 is able to perform simulations and employ some complex optimization algorithms to deliver an optimal treatment plan.

In one embodiment, the range information provided to the treatment planning software may be acceptable deviations from the dose volume constraints. For example, the PVT coverage may be between 95% and 107% and dose maximum below 112%.

In one embodiment, for example, the optimization engine 218 of the treatment planning software may run simulations to determine various irradiation times associated with a selected set of machine specific parameters. The optimization engine 218 may be programmed to determine the manner in which to vary the machine specific parameters in order to solve for the lowest irradiation times while maintaining an acceptable plan quality. In other words, the optimization engine 218 may be programmed to analyze the intermediate results and use them to more quickly converge towards a solution that yields the lowest irradiation times. In one embodiment, the optimization engine 218 may be programmed with one or several different optimization algorithms that allow the engine to converge to the most efficient solution without sacrificing plan quality.

In one embodiment of the present invention, based on the proton radiation therapy system, the machine configuration information including various machine parameters are accessed. The machine parameters may, for example, define a maximum resolution achievable by the proton radiation therapy system in irradiating a patient. The optimization engine, in one embodiment, may be configured to iteratively adjust the various machine parameters to generate one or more candidate treatment plans. The machine parameters can, for instance, be iteratively adjusted to values that decrease the maximum resolution. Subsequently, the various candidate treatment plans generated can be simulated in order to determine a respective treatment time and respective plan quality associated with each of the treatment plans. The optimization engine may then be programmed to select a candidate treatment plan that may yield an acceptable plan quality and the shortest possible treatment time.

Figure 3B:
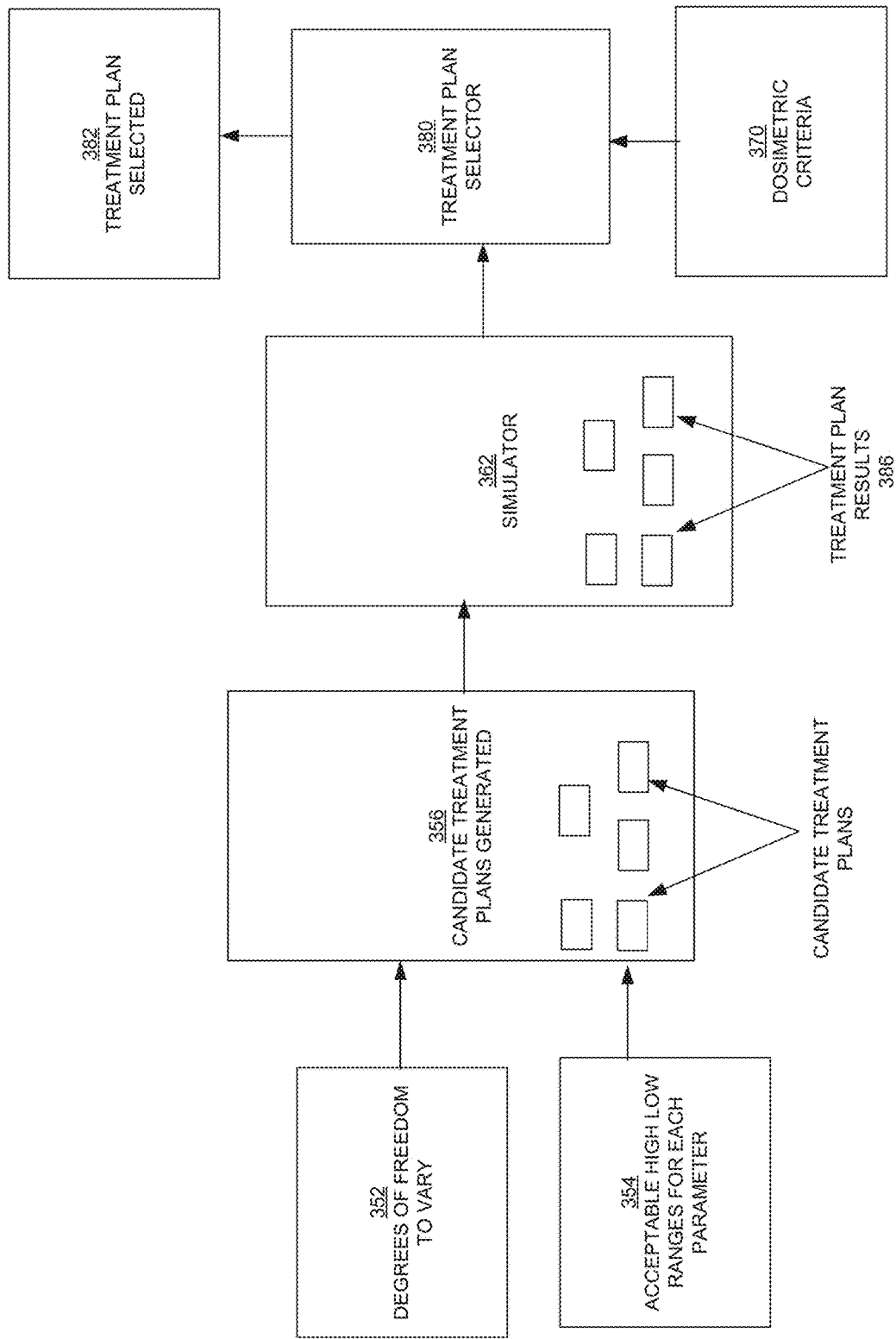
FIG. 3B illustrates a data flow diagram of a process that can be implemented to select a resultant treatment plans from a number of candidate treatment plants generated by varying machine specific parameters in accordance with an embodiment of the present invention.

FIG. 3B illustrates a data flow diagram of a process that can be implemented to select a resultant treatment plans from a number of candidate treatment plants generated by varying machine specific parameters in accordance with an embodiment of the present invention.

The various degrees of freedom to vary 352 and the acceptable high low ranges for each parameter 354 are used to generate a set of candidate treatment plans 356. Each candidate treatment plan may have a different value for each of the machine specific parameters (or degrees of freedom) but within a particular candidate treatment plan the value would be remain constant. For example, three different candidate treatment plans may be generated, where each of the candidate treatment plans would have a different value for the minimum number of MUs per spot, e.g., 3, 5 and 7 respectively. The simulator 362 of the optimization engine will subsequently generate a treatment plan result 386 for one or more of the candidate treatment plans. In one embodiment, the optimization engine may be able to converge on the most efficient solution without needing to simulate each and every one of the candidate treatment plans. Given the dosimetric criteria 370, the treatment plan selector 380 will then select the most time-efficient treatment plan 382 from amongst the result set.

For example, embodiments of the present invention allow the global minimum spot intensity (measured in Monitor Units or MUs) to be considered by the optimization process. In conventional systems, the global minimum spot intensity was fixed based on the beam machine. Embodiments of the present invention allow the minimum MUs per spot to vary in order to optimize for time constraints. For example, in some parts of the body it is beneficial to place spots that only deliver the minimum MUs. In other parts, however, placing many spots with low intensity confers no benefit with respect to dosimetric criteria over placing fewer spots with higher intensity. In other words, it may be faster and more efficient for some parts of the body to receive fewer spots with higher intensity rather than several spots with low intensity. For certain parts of the body, the treatment delivery system may use fewer spots with more MUs per spot—sacrificing resolution, while maintaining treatment plan quality allows the system to be more efficient.

By allowing the minimum MUs per spot to vary, the optimization engine 218 can optimize the treatment plan by delivering higher intensity at fewer spots on a patient (where permissible) rather than several different spots at lower intensity. Further, by reducing the total number of spots, the optimization engine can develop treatment plans with faster irradiation times and also improved dose homogeneity for the target structure, e.g., the tumor. For example, referring to the example provided above, if the minimum number of monitor units (MUs) per spot is specified to be 5 with a range of plus or minus 3, then the optimization engine may generate a number of candidate treatment plans where the minimum MUs per spot is varied from 2 MU to 8 MU between the various candidate treatment plans. After simulating the various treatment plans, the optimization engine may select the treatment plan that generates acceptable plan quality with the fastest possible treatment time.

Figure 4:
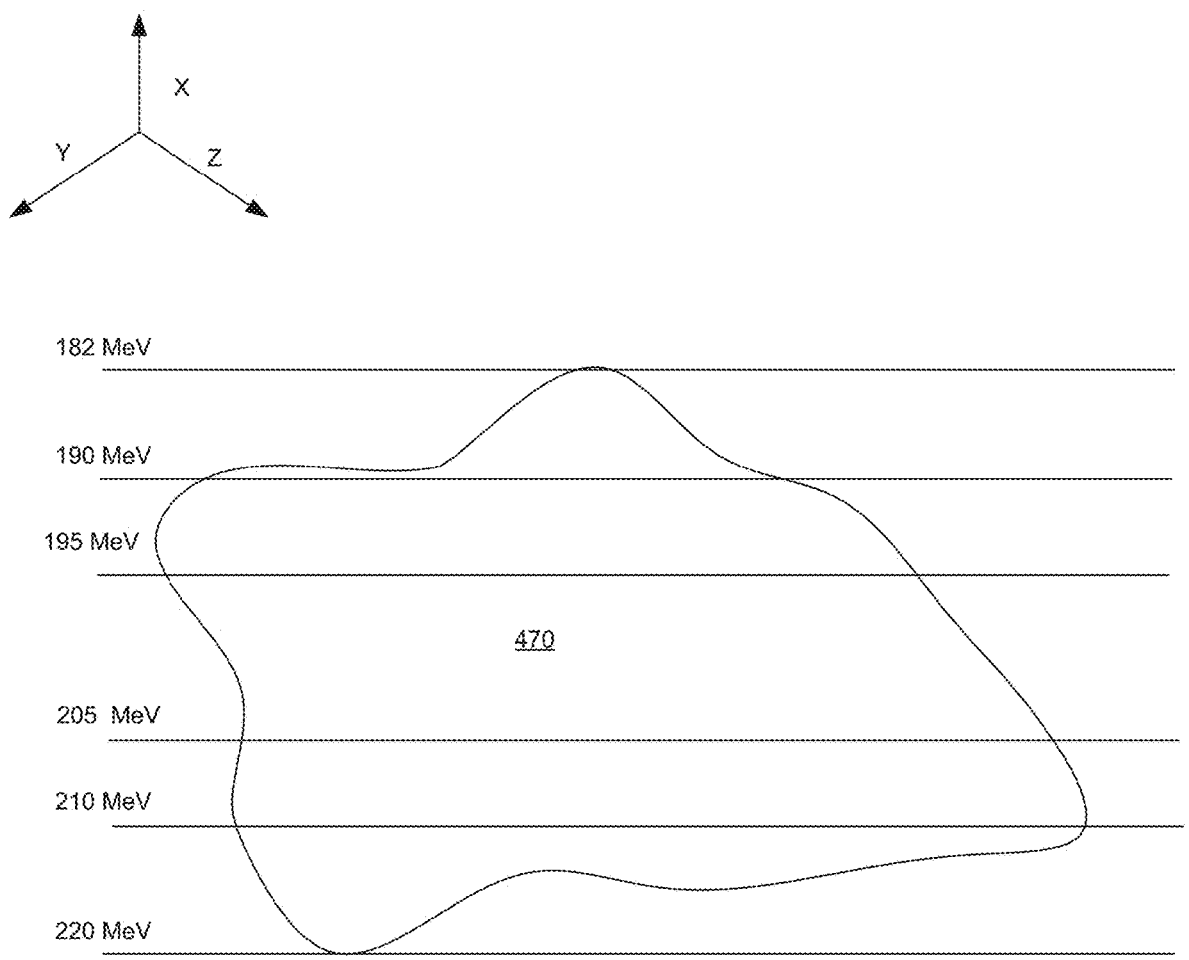
FIG. 4 illustrates the manner in which the resultant energies and steps between them can be optimized for in accordance with an embodiment of the present invention.

FIG. 4 illustrates the manner in which the resultant energies and steps between them can be optimized for in accordance with an embodiment of the present invention.

In IMRT, beam intensity is varied across each treatment region (target volume) in a patient. Instead of being treated with a relatively large and uniform beam, the patient is treated with many smaller beams (e.g., pencil beams or beamlets), each of which can have its own intensity, and each of which can be delivered from a different angle (which may be referred to as beam geometry). Because of the many possible beam geometries, the number of beams, and the range of beam intensities, there can effectively be an innumerable amount of potential treatment plans. In developing treatment plans, embodiments of the present invention use optimization engine 218 to select a treatment plan having the most efficient performance without sacrificing plan quality as mentioned above.

One of the beam machine specific parameters that can be optimized in accordance with an embodiment of the present invention is number of used energies and the spacing or distance between them. The energy level corresponds to the depth within the treatment region that the beam can reach. For example, an 180 MeV beam is able to irradiate a PTV at a higher depth than a 150 MeV beam. In conventional systems, the energy difference between adjacent/consecutive layers are fixed prior to any optimization using some scheme such as a fixed number of layers or a fixed layer spacing (which is the difference between consecutive energies, e.g., 3 MeV between each layer).

In one embodiment of the present invention, for example, the number of used energies and differences between consecutive energies can be considered as an additional parameter that can be varied between various candidate treatment plans. In other words, individual candidate treatment plans can have differences between energy levels in a delivery treatment field. As mentioned above, proton therapy can be limited by depth and, therefore, exposure to inadvertent radiation can be avoided or at least limited by non-target cells having a depth beyond a target calculated area. As mentioned above, in conventional treatment systems, the energy layer spacing (the difference between consecutive energy layers) was a fixed parameter and was associated with a fixed distance between each layer. For example, in a conventional treatment system, if the minimum depth of a target structure was 100 MeV and the maximum depth of the target structure was 200 MeV with a fixed 5 MeV layer spacing, then the treatment delivery system may deliver treatment at each 5 MeV increment between 100 MeV and 200 MeV (e.g., at 105 MeV, 110 MeV, 115 MeV, etc.)

By comparison, embodiments of the present invention allow the optimization engine to determine the number of energy levels (that need to be added between the maximum and minimum depth of the target structure) and the differences between consecutive energy levels (in a delivery treatment field) between them. For example, the treatment planning software may receive the minimum and maximum depth of treatment (based on the patient). Alternatively, the treatment planning software may also receive a range of acceptable energies. As shown in FIG. 4, the PTV may be between the ranges of 220 MeV and 182 MeV. Knowing the minimum and maximum depth (or acceptable range of energies), and the minimum and maximum number of energy layers it can deposit, the treatment planning software may generate a number of candidate treatment plans with varying depths and number of energy layers. Subsequently, the optimization engine may simulate one or more of the various candidate treatment plans and automatically perform an optimization to determine the optimal number of layers and the space between them. For example, for the PTV shown in FIG. 4, the optimization engine 218 may determine that the optimum number of layers is 4, spaced at 210 MeV, 205 MeV, 195 MeV and 190 MeV. Accordingly, as compared with conventional treatment planning systems, embodiments of the present invention are not restricted to a fixed number of layers or a fixed space between the layers (which can be inordinately time-intensive). The number of layers and the distance between consecutive layers can vary. The optimization engine will typically pick the number of layers and the layer spacing to minimize irradiation time while maintaining limits that guarantee accurate beam position and dose application.

In order to determine the optimum number of layers and the spacing between them, the optimization engine may need to conduct various simulations of multiple candidate treatment plans with varying energy levels. For example, the optimization engine may start at 182 MeV and vary the energy level by a constant value or a multiple of the value, e.g., an increment of 5 MeV or multiples of 5 MeV (across multiple candidate treatment plans) in order to determine the optimum number of layers and spacing. It may not need to simulate every possible treatment plan, because the optimization algorithm is configured to converge towards the most optimal solution after a certain number of simulations.

Embodiments of the present invention are also configured to vary the spot positions and spot lateral spread (spot size) over the various candidate treatment plans when optimizing for efficiency. As mentioned previously, in conventional systems, the spot size and the grid size over which the treatment is delivered was typically fixed. Embodiments of the present invention, however, allow for greater flexibility and efficiency by varying the spot size and spot position within acceptable ranges over multiple candidate treatment plans. For example, given the shape of the target (and associated positional limitations), the optimization engine can determine an optimal spot size and positions of the spots. As mentioned above, these parameters allow the treatment planning system to sacrifice the maximum resolution available for added efficiency. In other words, the radiation therapy system can iteratively adjust the spot positioning and spot lateral spread to find the optimal combination of resolution and efficiency.

FIGS. 5A and 5B illustrate exemplary grids in the x-y plane within an energy level over which proton therapy is delivered in accordance with an embodiment of the invention. As seen in FIG. 5B the spot lateral spread is larger than in FIG. 5A. Since the spot size and spot spacing (or spot positioning) parameters are related, the larger the spot size, the narrower the spacing required between the spots. Embodiments of the present invention allow the spot size and spot spacing to be set at optimal levels so that the required dose can be delivered adequately in the fastest amount of time possible. For example, in one particular treatment, instead of delivering proton therapy at the two spots 510 and 520 (shown in FIG. 5A), the treatment planning software may determine it is equally effective and more efficient to simply direct the dose energy towards a single larger spot 530. In such an instance, for example, the irradiation time may be minimized because the optimization engine allows fewer, larger-sized spots to be irradiated as opposed to several, smaller spots.

In one aspect of the invention, the spot positions can be varied over multiple candidate treatment plans so that the spots do not need to conform to a fixed grid. In conventional treatment systems, because the spot size and spot spacing parameters were fixed, the spots needed to conform to a fixed grid. Embodiments of the present invention allow the spot lateral spread and spot positioning parameters to freely vary (within acceptable ranges) between multiple candidate treatment plans and, therefore, there is no need for the spots to conform to a fixed grid. For example, as seen in FIG. 5A, spot 585 does not conform to the fixed grid.

Figure 6:
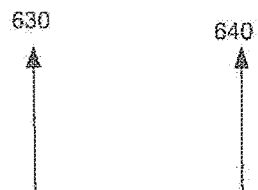
FIG. 6 is a table illustrating a plurality of candidate treatment plans and their results, wherein each cell of the table is representative of a radiation machine model implemented by the optimization engine to determine irradiation time and plan quality for a respective treatment plan in accordance with an embodiment of the invention.

FIG. 6 is a table illustrating a plurality of candidate treatment plans and their results, wherein each cell of the table is representative of a radiation machine model implemented by the optimization engine to determine irradiation time and plan quality for a respective treatment plan in accordance with an embodiment of the invention.

As shown in the table of FIG. 6, the minimum MUs per spot and the energy layer spacing were adjusted to develop multiple candidate treatment plans (for three fields, field 1, field 2 and field 3). Each of the cells indicated in the table shown in FIG. 6 comprises a result of a simulation associated with a respective treatment plan. Each cell, for example, presents the time duration (number of seconds) it took for the treatment delivery system to perform a respective simulation associated with the corresponding setting of energy layer spacing and minimum MUs per spot.

As seen in FIG. 6, grid 630 displays time-based results for all the associated candidate treatment plans that met all the criteria for treatment plan quality, e.g., PTV coverage, dose maximum, etc. The other candidate treatment plans fail in one or more plan quality criterion. Furthermore, out of those, grid 640 displays results for all treatment plans that could be conducted in the shortest time periods while maintaining an acceptable plan quality. In this example, the treatment plan 640 would be the output of the optimization engine 218.

The optimization engine 218 would, similarly, for all the degrees of freedom, conduct various simulations by varying the machine parameters within acceptable ranges to determine treatment times and corresponding plan qualities for various candidate treatment plans. In most instances, the optimization engine may not need to conduct every possible simulation, but may be able to converge to the most efficient solution (with acceptable plan qualities) using optimization algorithms.

As discussed in connection with FIG. 3B, the various degrees of freedom to vary 352 and the acceptable high low ranges for each parameter 354 are used to generate a set of candidate treatment plans 356. For example, in the table of FIG. 6, candidate treatment plans would be generated for each combination of minimum MUs per spot (e.g., 3 MU, 5 MU, 8 MU and 11 MU) and energy layer spacing (3 MeV, 5 MeV, 8 MeV, and 11 MeV). Each candidate treatment plan may have a different value for each of the machine specific parameters (or degrees of freedom) but within a particular candidate treatment plan the value would be remain constant.

Referring back to the table in FIG. 6, for example, a candidate treatment plan may be generated that uses a minimum 3 MUs per spot with an energy layer spacing of 3 MeV—within this particular candidate treatment plan the MUs per spot and energy layer spacing would be held constant. The simulator 362 of the optimization engine will subsequently generate a treatment plan result 386 for one or more of the candidate treatment plans. As mentioned above, in one embodiment, the optimization engine may be able to converge on the most efficient solution without needing to simulate each and every one of the candidate treatment plans. In other words, during treatment planning in the field, the optimization engine may not need to generate results for each possible combination of minimum MUs per spot and energy layer spacing.

Given the dosimetric criteria 370, the treatment plan selector 380 will then select the most time-efficient treatment plan 382 from amongst the result set. In the example of FIG. 6, resultant plan 640 would be determined to be the most time-efficient treatment plan from amongs the result set.

In one embodiment, the treatment planning software may comprise a graphical user interface (GUI) that calculates and displays the field irradiation times during optimization. Further, the GUI may allow users to place objectives and priorities on delivery time for each treatment field. Also, the GUI may allow the user to vary field-specific machine parameters in the optimization interface e.g., spot lateral spread, minimum number of MUs per spot etc.

Figure 7:
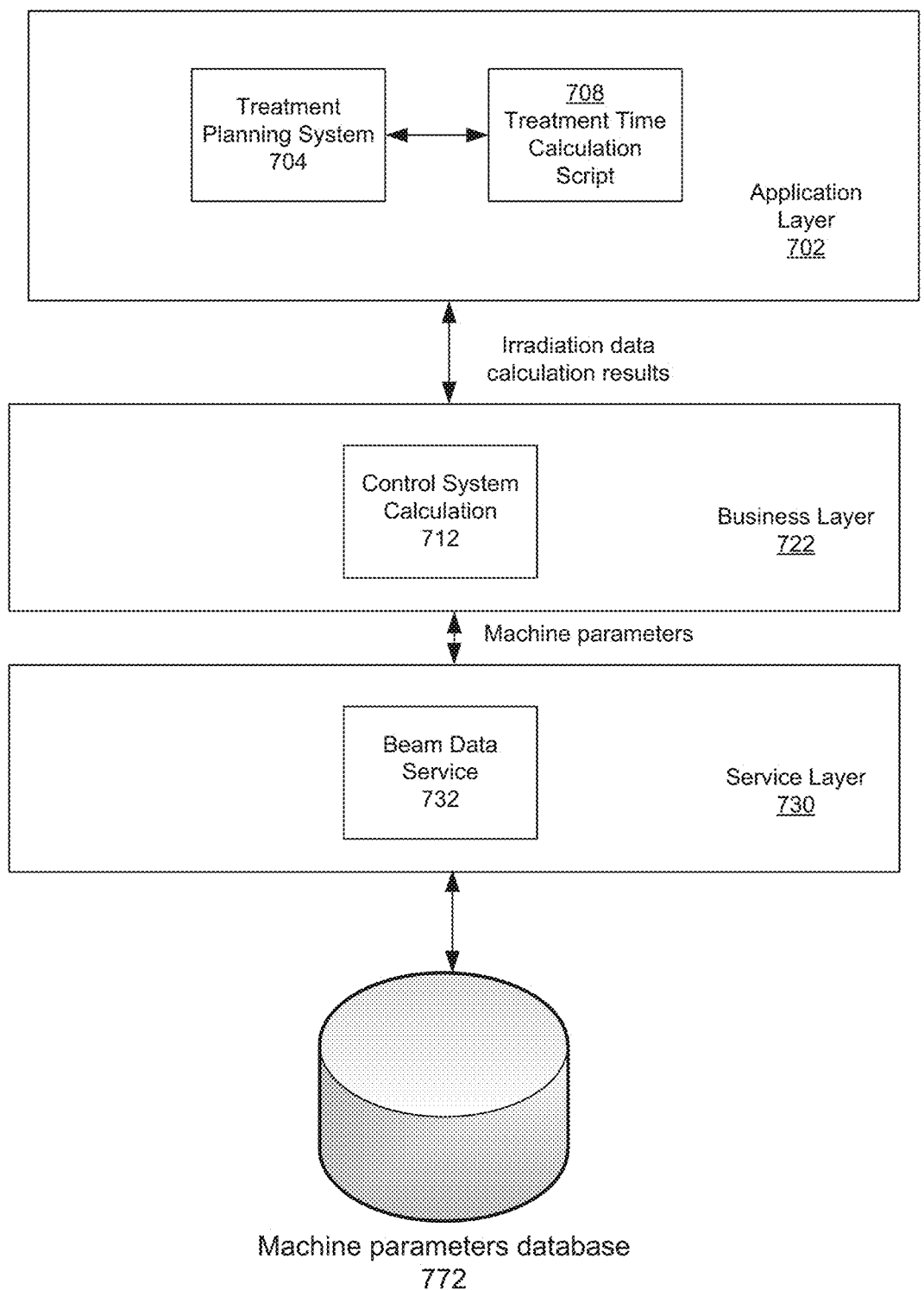
FIG. 7 is a high-level software flow diagram illustrating the manner in which machine specific parameters are used in the treatment planning system to determine the most efficient treatment plans in accordance with an embodiment of the present invention.

FIG. 7 is a high-level software flow diagram illustrating the manner in which machine specific parameters are used in the treatment planning system to determine the most efficient treatment plans in accordance with an embodiment of the present invention.

The treatment planning software system receives the machine parameters into the beam data service module 732 from the machine parameters database 772 into the service layer 730. The machine parameters are then transmitted to the business layer 722 where the control system 712 performs the calculations of the various treatment plans with the machine parameters. The irradiation data determined by the control system calculation module 712 are transmitted to the application layer 702. In the application layer, the treatment planning system 704 uses the irradiation data to determine the treatment times using module 708. Once treatment time calculation script 708 determines treatment time, the treatment planning system can select a treatment that has the most efficient times while maintaining acceptable plan quality.

Figure 8:
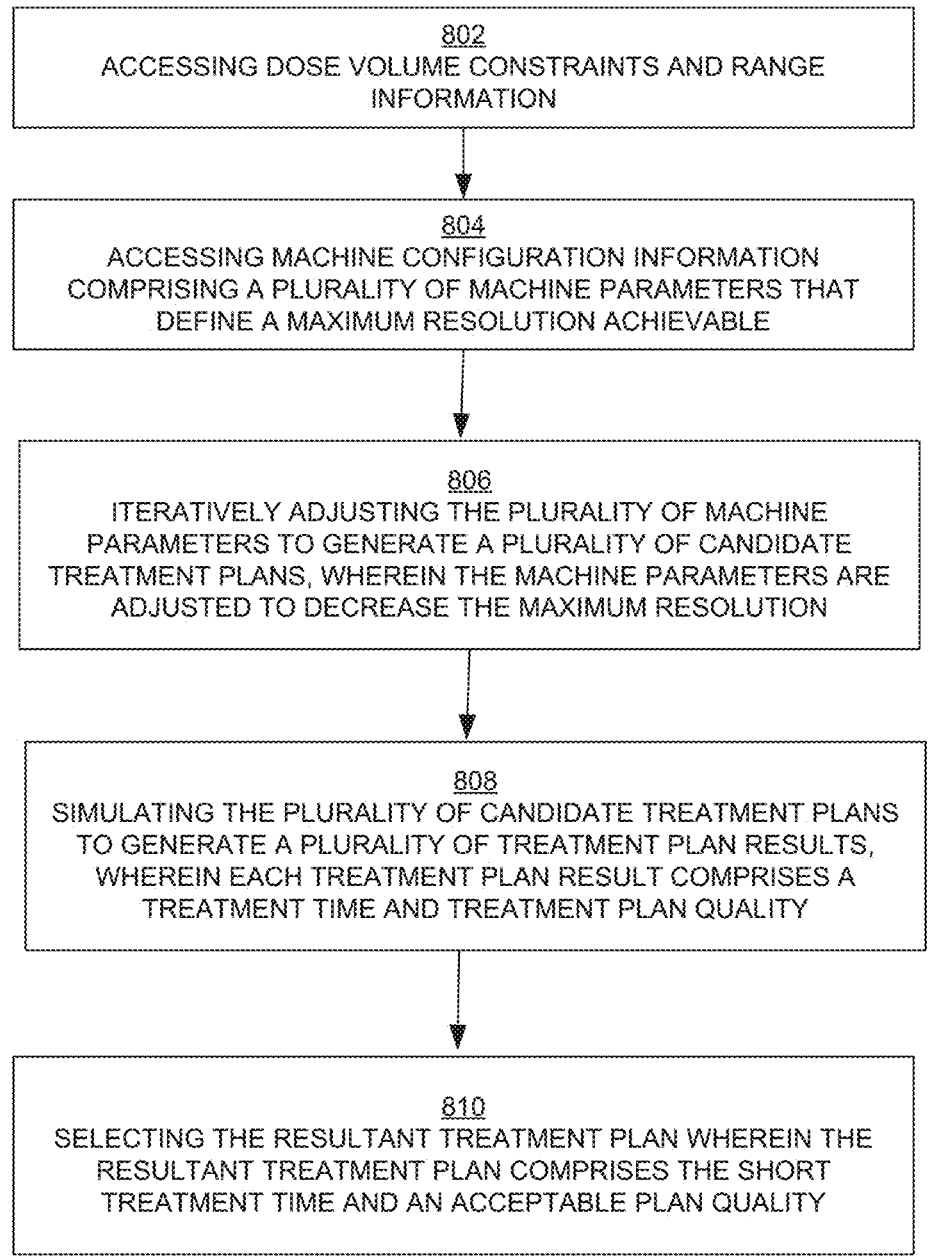
FIG. 8 is a flowchart depicting another exemplary process flow for determining a resultant treatment plan for a proton radiation therapy system based on given dose volume constraints, wherein the resultant plan is optimized for treatment time, in accordance with an embodiment of the present invention.

FIG. 8 is a flowchart depicting another exemplary process flow 800 for determining a resultant treatment plan for a proton radiation therapy system based on given dose volume constraints, wherein the resultant plan is optimized for treatment time, in accordance with an embodiment of the present invention.

At step 802, the dose volume constraints and range information is accessed, wherein the range information indicates acceptable deviations from the dose volume constraints. As mentioned above, the minimum and maximum range of machine specific parameters may also be provided to the treatment planning software to perform the optimization.

At step 804, based on said proton radiation therapy system, machine configuration information is accessed comprising a plurality of machine parameters that define a maximum resolution achievable by the proton radiation therapy system in irradiating a patient. In other words, the machine parameters can be varied to achieve a maximum possible resolution in irradiating a patient—however, the same parameters can also be varied to deliver the treatment to the patient in the shortest amount of time by trading off the maximum resolution for efficiency.

At step 806, the optimization engine of the treatment planning software iteratively adjusts the plurality of machine parameters to generate a plurality of candidate treatment plans, wherein the iteratively adjusting comprises adjusting the plurality of machine parameters to values which decrease the maximum resolution. Decreasing the maximum resolution, for example, may result in faster performance.

At step 808, the optimization engine simulates the plurality of candidate treatment plans with respect to the proton radiation therapy system to generate a plurality of treatment plan results, wherein each treatment plan result comprises a respective treatment time and a respective plan quality. As shown in FIG. 6, for each treatment plan simulated, a time value can be obtained to indicate the amount of time it would take to deliver the respective treatment.

Finally, at step 810, the optimization engine selects the resultant treatment plan from the plurality of candidate treatment plans, wherein the resultant treatment plan yields a treatment plan result comprising a shortest treatment time of the plurality of treatment plan results and an acceptable plan quality with respect to the dose volume constraints.

Embodiments according to the invention are thus described. These embodiments can be used to plan different types of external beam radiotherapy other than IMRT including, for example, image-guided radiotherapy (IGRT), RapidArc™ radiotherapy, stereotactic body radiotherapy (SBRT), and stereotactic ablative radiotherapy (SABR).

Furthermore, embodiments of the present invention perform a multi-directional optimization that optimizes a treatment plan for efficiency by considering complex machine and beam-specific parameters (e.g., minimal application monitor units per spot, energy layer spacing, spot size and spot spacing, etc.) without sacrificing plan quality—performing such a multi-directional optimization is beyond the capability of a human and requires the use of a computing system. Embodiments according to the invention allow effective treatment plans with low treatment delivery times to be generated, which limit the possibility of irregularities or inaccuracies in treatment delivery resulting from patient movement. By optimizing for efficiency and time-based constraints, embodiments according to the invention help

What is claimed is:

1. A computer implemented method of determining a resultant treatment plan for a proton radiation therapy system based on given dose volume constraints, wherein said resultant treatment plan is optimized for treatment time, said method comprising:
   accessing said dose volume constraints and range information, wherein said range information indicates acceptable deviations from said dose volume constraints;
   based on said proton radiation therapy system, accessing machine configuration information comprising a plurality of machine parameters operable to be varied to achieve a maximum resolution by said proton radiation therapy system in irradiating a patient, wherein said plurality of machine parameters are associated with beam characteristics of a beam machine of the proton radiation therapy system, and wherein said machine configuration information comprises a different range for each of the plurality of machine parameters;
   iteratively adjusting said plurality of machine parameters to generate a plurality of candidate treatment plans, wherein said iteratively adjusting comprises adjusting said plurality of machine parameters to values which decrease said maximum resolution;
   simulating said plurality of candidate treatment plans with respect to said proton radiation therapy system to generate a plurality of treatment plan results, wherein each treatment plan result comprises: a respective treatment time and a respective plan quality, wherein said simulating comprises conducting one or more simulations using values selected across a respective range for each of the plurality of machine parameters; and
   selecting said resultant treatment plan from said plurality of candidate treatment plans, wherein said resultant treatment plan yields a treatment plan result comprising: a shortest treatment time of said plurality of treatment plan results and an acceptable plan quality with respect to said dose volume constraints and said range information.

2. A method as described in claim 1 wherein said plurality of machine parameters comprise: minimal monitor unit (MU) per spot; and number of available energies.

3. A method as described in claim 2 wherein said plurality of machine parameters further comprise a spot lateral spread.

4. A method as described in claim 3 wherein said plurality of machine parameters further comprise a spot positioning.

5. A method as described in claim 1 wherein said acceptable plan quality is defined as a plan quality that deviates from said dose volume constraints within said range information.

6. A method as described in claim 1 further comprising:
   loading said resultant treatment plan into said proton radiation therapy system; and
   using said proton radiation therapy system, as configured by said resultant treatment plan, to irradiate a patient.

7. A method as described in claim 1 wherein said range information comprises:
   planning target volume (PTV) coverage between a lower bound percentage and an upper bound percentage; and
   dose maximum below a bound percentage.

8. A computer system comprising a processor coupled to a bus and memory coupled to said bus wherein said memory is programmed with instructions that when executed cause said computer system to implement a method of determining a resultant treatment plan for a proton radiation therapy system based on given dose volume constraints, wherein said resultant treatment plan is optimized for treatment time, wherein said method comprises:
   accessing said dose volume constraints and range information, wherein said range information indicates acceptable deviations from said dose volume constraints;
   based on said proton radiation therapy system, accessing machine configuration information comprising a plurality of machine parameters operable to be varied to achieve a maximum resolution by said proton radiation therapy system in irradiating a patient, wherein said plurality of machine parameters are associated with constraints related to a beam machine of the proton radiation therapy system, and wherein said machine configuration information comprises a different range for each of the plurality of machine parameters;
   iteratively adjusting said plurality of machine parameters to generate a plurality of candidate treatment plans, wherein said iteratively adjusting comprises adjusting said plurality of machine parameters to values which decrease said maximum resolution;
   simulating said plurality of candidate treatment plans with respect to said proton radiation therapy system to generate a plurality of treatment plan results, wherein each treatment plan result comprises: a respective treatment time; and a respective plan quality, wherein said simulating comprises conducting one or more simulations using values selected across a respective range for each of the plurality of machine parameters; and
   selecting said resultant treatment plan from said plurality of candidate treatment plans, wherein said resultant treatment plan yields a treatment plan result comprising: a shortest treatment time of said plurality of treatment plan results; and an acceptable plan quality with respect to said dose volume constraints and said range information.

9. A system as described in claim 8 wherein said plurality of machine parameters comprise: minimal monitor unit (MU) per spot; and number of available energies and steps between the available energies.

10. A system as described in claim 9 wherein said plurality of machine parameters further comprise a minimal spot size.

11. A system as described in claim 10 wherein said plurality of machine parameters further comprise a minimal spot spacing.

12. A system as described in claim 8 wherein said acceptable plan quality is defined as a plan quality that deviates from said dose volume constraints within said range information.

13. A system as described in claim 8 further comprising said proton radiation therapy system and wherein said method further comprises:
   loading said resultant treatment plan into said proton radiation therapy system; and causing said proton radiation therapy system, as configured by said resultant treatment plan, to irradiate a patient.

14. A system as described in claim 8 wherein said range information comprises:
   planning target volume (PTV) coverage between a lower bound percentage and an upper bound percentage; and
   dose maximum below a bound percentage.

15. A computer implemented method of determining a treatment plan for proton radiation therapy that is optimized for treatment time, said method comprising:
   accessing information defining patient anatomy, dosimetric criteria and delivery system properties, wherein said dosimetric criteria comprises dose volume constraints and range information, wherein said range information indicates acceptable deviations from said dose volume constraints;
   based on a proton radiation therapy system, accessing delivery system properties comprising a plurality of machine parameters that configure said proton radiation therapy system to achieve a resultant resolution, wherein said plurality of machine parameters are associated with beam characteristics related of a beam delivered by the proton radiation therapy system, and wherein said delivery system properties comprises a different range for each of the plurality of machine parameters;
   iteratively adjusting said plurality of machine parameters to generate a plurality of candidate treatment plans, wherein said iteratively adjusting comprises adjusting said plurality of machine parameters to values which decrease a maximum resolution achievable by said proton radiation therapy system;
   simulating said plurality of candidate treatment plans with respect to said proton radiation therapy system to generate a plurality of treatment plan results, wherein each treatment plan result comprises: a respective treatment time; and a respective plan quality, wherein said simulating comprises conducting one or more simulations using values selected across a respective range for each of the plurality of machine parameters; and
   selecting said treatment plan from said plurality of candidate treatment plans, wherein said treatment plan yields a treatment plan result comprising: a shortest treatment time of said plurality of treatment plan results; and an acceptable plan quality with respect to said dose volume constraints and said range information.

16. A method as described in claim 15 wherein said plurality of machine parameters comprise: beam energy; spot position; spot intensity; and spot lateral spread.

17. A method as described in claim 15 wherein said plurality of machine parameters comprise: beam energy; and spot intensity.

18. A method as described in claim 17 wherein said acceptable plan quality is defined as a plan quality that deviates from said dose volume constraints within said range information.

19. A method as described in claim 17 further comprising:
   loading said treatment plan into said proton radiation therapy system; and
   using said proton radiation therapy system, as configured by said treatment plan, to irradiate a patient.

20. A method as described in claim 17 wherein said range information comprises:
   planning target volume (PTV) coverage between a lower bound percentage and an upper bound percentage; and
   dose maximum below a bound percentage.

* * * * *